Figure 1:
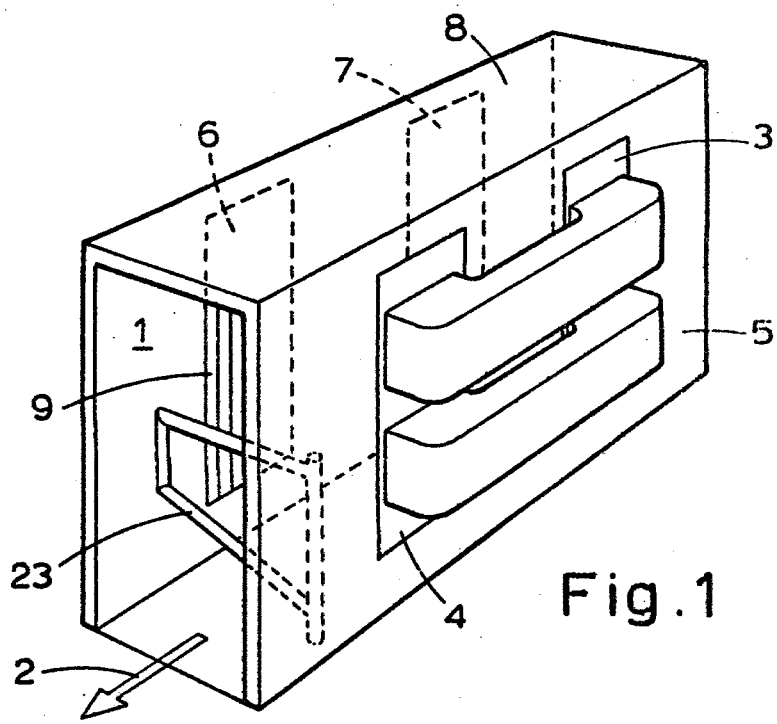

United States Patent [19]

Ellson

[11] 4,202,200
[45] May 13, 1980

[54] APPARATUS FOR DETECTING EXPLOSIVE SUBSTANCES

[75] Inventor: Allan H. Ellson, Harpenden, England

[73] Assignee: Pye (Electronic Products) Limited, Cambridge, England

[21] Appl. No.: 951,557

[22] Filed: Oct. 16, 1978

Related U.S. Application Data

[63] Continuation of Ser. No. 810,665, Jun. 28, 1977, abandoned.

[30] Foreign Application Priority Data

Jul. 1, 1976 [GB] United Kingdom ............... 27447/76

[51] Int. Cl.² .............................................. G01N 31/00
[52] U.S. Cl. ....................................................... 73/23
[58] Field of Search ........................... 73/23, 421.5 R; 340/632, 633, 634

[56] References Cited

U.S. PATENT DOCUMENTS 3,998,101  12/1976  Bradshaw et al. ............... 73/421.5 R
4,045,997   9/1977  Showalter et al. ...................... 73/23

Primary Examiner—Stephen A. Kreitman
Attorney, Agent, or Firm—Thomas A. Briody; Paul R. Miller

[57] ABSTRACT

An apparatus for detecting the presence of explosives by screening subjects passing through a controlled axis tunnel, the apparatus comprising a substantially open ended tunnel having a cross-section so that subjects can proceed in a single file through the tunnel. The apparatus further comprises a first pair of apertures, one in each side wall of the tunnel located at a first distance from an entrance to the tunnel, and a second pair of apertures, one in each side wall of the tunnel, located at a second distance greater than the first distance from the entrance to the tunnel. Air duct means extend between the various apertures. Also included are means for inducing a circulatory flow of air through the air duct means and across the tunnel between the apertures and, further, means for detecting the vapor of an explosive substance in the air in such duct means.

8 Claims, 2 Drawing Figures

U.S. Patent  May 13, 1980  4,202,200

APPARATUS FOR DETECTING EXPLOSIVE SUBSTANCES

This is a continuation, of application Ser. No. 810,665, filed June 28, 1977, now abandoned.

This invention relates to an apparatus for detecting the presence of explosive substances and more particularly to an apparatus for screening subjects, such as persons and/or vehicles, passing through a controlled access tunnel or gateway for the possession of explosives, as for example in the control of terrorist activities.

For the purpose of the present invention an explosive substance is defined as any substance which is capable of being transformed by a sudden expansion of gas into a volume much greater than its initial volume and which substance emits a detectable vapour at normal temperatures and pressures characteristic of the explosive substance. Such explosive substances, include gelignite, nitroglycerine, dynamite and others such as, methyl nitrate, trinitrotoluene and ammonium nitrate each of which emit characteristic vapours. These vapours are heavy and "sticky" and tend to become attached to any material in contact with or wrapped round the explosive. In particular the vapour tends to become attached to the clothing of a person who is or has been carrying explosives. Similarly vapour becomes attached to the bodywork and upholstery of a car used for carrying explosives.

Detection apparatus (of the so-called "explosives sniffers" type) are known as being capable of responding to the vapours emitted by explosive substances. In such devices, a finite sample of air is drawn through a sensing probe into the detector for analysis, and an indication is given if an explosives vapour is present in the sample, even in low concentration. If the sensing probe of the explosives detector is moved over the clothing of a person who is or has been carrying explosives, the vapour attached to the clothing will be detected and an alarm can be given.

A vehicle which is or has been carrying explosives may also be detected by passing the probe over the bodywork and upholstery.

This method, although successful in detecting explosives substances, has several disadvantages, particularly when large numbers of subjects (persons or vehicles) have to be screened. Prior to the present invention each subject had to be examined separately by an operator using a portable explosives detector and the method was labour intensive and liable to cause substantial delays.

One object of the present invention is to provide an apparatus which can screen large numbers of subjects in a simple and efficient manner. Persons being screened found the procedure embarrassing or otherwise objectionable. A further object of the invention is to provide an apparatus which examines subjects in an automatic manner when subjects, such as, passengers or vehicles are caused to pass through a tunnel or passageway for a predetermined period of time. During this predetermined period of time the subjects may be caused to halt one or more times in the tunnel or gateway.

According to the present invention there is provided an apparatus for detecting the presence of explosives by screening subjects passing through a controlled access tunnel comprising a substantially open ended tunnel having a cross-section so that subjects can proceed in a single file through the tunnel, a first pair of apertures, one in each side wall of the tunnel located at a first distance from an entrance to the tunnel, a second pair of apertures, one in each side wall of the tunnel, located at a second distance, greater than the first distance from the entrance of the tunnel, first air duct means extending between the first aperture of the first pair and a first aperture of the second pair, second air duct means extending between a second aperture of said first pair and a second aperture of said second pair, means for inducing a circulatory flow of air through said first air duct means, across the tunnel between the apertures of said first pair, through said second air duct means, and across the tunnel between the apertures of said second pair, and means for detecting the vapour of an explosive substance in the air in at least one of said duct means. The means for detecting the vapour of the explosive substance in the air may be located in both the first air duct means and in the second air duct means. The means for inducing the circulatory flow of air through said first air duct means may comprise at least one air impellor located in said first air duct means.

The second air duct may contain additionally at least one air impellor.

In one embodiment the first aperture of the first pair of apertures is sub-divided into two or more smaller apertures, and the first aperture of the second pair of apertures is sub-divided into two or more smaller apertures, each of the first small apertures being separately connected to a corresponding small first aperture of the second pair by air duct means. In another embodiment the second aperture of the first pair of apertures is sub-divided into two or more smaller apertures, and the second aperture of the second pair of apertures is sub-divided into two or more smaller apertures, each of the small second apertures of the first pair being separately connected to corresponding small second aperture of the second pair.

In the case of foot passengers there is provided a tunnel or gateway wide enough to admit one person at a time, each person to be screened being required to pass through the tunnel or gateway, where the person may be caused to stop for a set period of time, i.e., within the circulatory flow of air before moving on.

Explosives vapour stripped from the person by the air stream, in general is entrained in the air stream only in low concentration, but, because of the circulatory flow of air, does not become further diluted to the detriment of the sensitivity of the system before it reaches the detector.

In order that the invention and the way in which it is to be performed may be clearly understood, an embodiment thereof will be described, by way of example with reference to the attached drawings, of which:-

Figure 2:
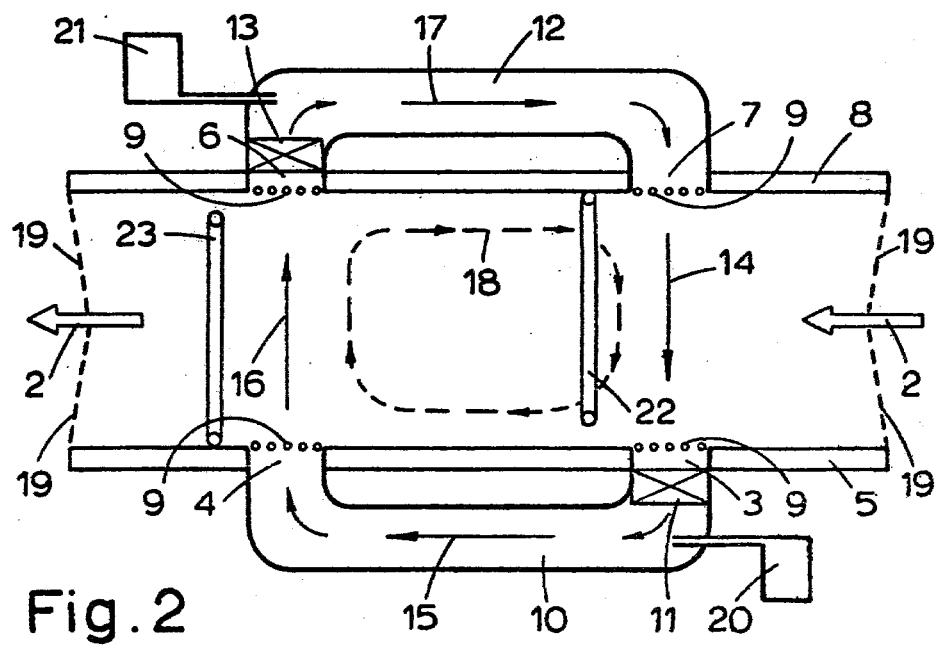

FIG. 1 is a perspective view of a screening gateway according to the invention and FIG. 2 is a plan view of the arrangement of FIG. 1.

Referring to the drawings, access to a protected area is obtained through a passageway or tunnel 1. For foot passengers the tunnel may typically be 3 ft. wide, 7 ft. high and 10 ft. long. Foot passengers will therefore traverse the tunnel, in the direction indicated by the arrows 2, substantially in single file.

Apertures 3 and 4 are provided in a side wall 5 of the tunnel 1, and similar apertures 6 and 7 are provided in the opposite side wall 8, the arrangement being such that the aperture 6 is opposite the aperture 4, the aperture 7 opposite the aperture 3, and the two pairs of opposed apertures are separated by a distance of, e.g., four feet, measured along the tunnel 1.

Typically each aperture may be approximately one foot wide and five feet high. Optionally, each aperture may be sub-divided into a plurality of separate smaller apertures, each of which may be at different heights. Grills 9 may be provided at the mouths of each of the smaller apertures.

Outside the wall 5, one or more ducts 10 extend from the aperture 3 to the aperture 4. A fan 11 is provided with each associated duct 10 behind the aperture 3, arranged to draw air through the aperture 3 and to impel it along the duct or ducts 10 to the aperture 4.

A similar arrangement of one or more ducts 12 extends from the aperture 6 to the aperture 7. A fan 13 or air impeller, is provided with each associated duct 12 to draw air in through the aperture 6 and impel it along the duct or ducts 12 and out of the aperture 7. The arrangement is such that the air in the system circulates continually through the ducts 10 and 12 and across the tunnel 1 as indicated by the arrows 14, 15, 16, 17. In addition, a rotating air pattern is set up in the middle of the tunnel indicated by the broken line 18. Because of the symmetry of the arrangement very little air is drawn in or escapes from the ends of the tunnel. If it is desired to reduce still further the quantity of air entering or leaving the system, swing doors, indicated in FIG. 2 by the broken lines 19 may be provided at the ends of the tunnel 1. In an alternative embodiment the rotating air may circulate, at least in part, through the ducts 10 and 12 and across the tunnel 1 in a non-horizontal direction whence one aperture may be located in a wall other than a side wall and another aperture located in an opposite wall. In this manner normal convection currents may be caused to assist the circulation of the air under examination.

When a person enters the tunnel and moves into the area of the air stream 14, some of the heavy explosive vapour when present and which may be clinging to his clothing and/or skin or to the wrappings of an explosive substance which he may be carrying is blown off and collected by the fans 11 to pass into the duct or ducts 10. In traversing the tunnel, the person is also exposed to the air stream 16 when further samples of vapour are blown off and collected by the fan 13 to pass into the duct or ducts 12. One or a number of explosives vapour detectors such as described in our co-pending patent application No. 10054/75 and known as Pye Dynamics Limited Type PD2 to sample the air may be provided in duct 10 and in 12, and are indicated schematically in FIG. 2 at 20 and 21. These are arranged to trigger an alarm if explosives vapour is detected.

Optionally, movable barriers 22 and 23 may be provided, to prevent the subject traversing the tunnel 1 faster than a predetermined rate speed. The barriers 22 and 23 may ensure that the person pauses momentarily in the air streams 14 and 16 while opening the barriers. Optionally also, the barriers 22 and 23 may be locked in the closed position or other constraints or barriers not shown in the drawing may be actuated if explosives vapour is detected by the detectors 20 and/or 21.

A similar arrangement may be employed for screening cars and other light vehicles. In this case the tunnel 1 may typically be seven feet wide and eight feet high, so as to accept the vehicles one at a time. The length of the tunnel may be e.g. twenty five feet. The distance between the pairs of apertures 3, 4 and 6, 7 may be say fifteen feet and the size of the apertures and cross-section of the ducts may be increased pro rata. The barriers 22 and 23 may be of the automatic type, opening only when a vehicle approaches closely to them.

I claim:

1. An apparatus for detecting the presence of explosives by screening subjects passing through a controlled access tunnel, comprising:
   (a) a substantially open ended tunnel having a cross-section so that subjects can proceed in a single file through the tunnel, said tunnel comprising side walls and an entrance;
   (b) a first pair of apertures, one of each of said apertures of said first pair being located in each respective said side wall of the tunnel, located at a first distance from said entrance to the tunnel;
   (c) a second pair of apertures, one of each of said apertures of said second pair being located in each respective said side wall of the tunnel and located at a second distance greater than the first distance from the entrance to the tunnel;
   (d) first air duct means extending between a first aperture of said first pair and a first aperture of said second pair;
   (e) second air duct means extending between a second aperture of said first pair and second aperture of said second pair;
   (f) means for inducing a circulatory flow of air through said first air duct means, across the tunnel between the apertures of said first pair, through said second air duct means and across the tunnel between the apertures of said second pair; and
   (g) means for detecting the vapor of an explosive substance in the air in at least one of said duct means.

2. An apparatus according to claim 1 in which the means for detecting the vapor of the explosive substance in the air is located in both the first air duct means and in the second air duct means.

3. An apparatus according to claim 1 in which the means for inducing the circulatory flow of air through said first air duct means comprises at least one air impellor located in said first air duct means.

4. An apparatus according to claim 2 in which the second air duct means contains at least one air impellor.

5. An apparatus according to claim 1 in which the first aperture of the first pair of apertures is sub-divided into two or more smaller apertures, and the first aperture of the second pair of apertures is sub-divided into a two or more smaller apertures, each of the first small apertures of said first pair being separately connected to a corresponding small first aperture of the second pair by air duct means.

6. An apparatus according to claim 1 in which the second aperture of the first pair of apertures is sub-divided into two or more smaller apertures, and the second aperture of the second pair of apertures is sub-divided into two or more smaller apertures, each of the small second apertures of the first pair being separately connected to a corresponding small second aperture of the second pair.

7. An apparatus according to claim 1 in which the tunnel contains one or more barriers to temporarily prevent the subjects from passing freely past the first pair and the second pair of apertures.

8. An apparatus according to claim 1 in which the tunnel has an entrance with an air baffle door and an exit with an air baffle door.

* * * * *